United States Patent [19]

Nagatomo

[11] Patent Number: 5,807,218

[45] Date of Patent: Sep. 15, 1998

[54] LIMB POSITIONING DEVICE

[76] Inventor: Yasuaki Nagatomo, 215 Serenity Ct. SE., Albuquerque, N. Mex. 87123

[21] Appl. No.: 873,574

[22] Filed: Jun. 12, 1997

[51] Int. Cl.[6] ........................... A63B 21/02; A63B 21/00; A63B 69/00; A61F 5/37

[52] U.S. Cl. .......................... 482/124; 482/131; 482/126; 473/458; 128/869; 128/876

[58] Field of Search ..................................... 482/124, 125, 482/126, 121, 74, 139; 434/255, 252; 473/458, 217; 128/869, 876

[56] References Cited

U.S. PATENT DOCUMENTS

| | | |
|---|---|---|
| 1,677,728 | 7/1928 | Robinson . |
| 2,224,103 | 12/1940 | Nilson ...................................... 482/124 |
| 4,544,155 | 10/1985 | Wallenbrock ........................ 482/139 X |
| 4,757,995 | 7/1988 | Gallagher . |
| 4,815,731 | 3/1989 | Suarez et al. . |
| 4,911,434 | 3/1990 | Herring ................................ 482/139 X |
| 5,016,885 | 5/1991 | Quigley . |
| 5,020,796 | 6/1991 | Ullmann .............................. 482/139 X |
| 5,263,916 | 11/1993 | Bobich . |
| 5,336,151 | 8/1994 | Van Ballegooie . |
| 5,518,486 | 5/1996 | Sheeler ................................ 482/139 X |
| 5,614,300 | 3/1997 | Cicali .................................. 482/124 X |

Primary Examiner—Richard J. Apley
Assistant Examiner—William LaMarca
Attorney, Agent, or Firm—John R. Lansdowne

[57] ABSTRACT

A combination stance limiting and muscle flexing device particularly useful in karate training. The device consists of a flexible strap which is adjustable in total length, connected at opposite ends by means of swivel connectors with cuff assemblies to be worn on the legs or arms of an individual. The flexible strap is made up of two length-adjustable portions connected by an elastic portion. The length-adjustable portions form loops at their free ends which receive the swivel connectors and are adjusted by folding the strap material over on itself at selected positions along the body of the strap material. The strap material is made of Velcro material which easily attaches and detaches to allow for easy adjustment. The elastic portion of the strap allows a limited stretch capability of about two inches. Once the student's limbs are at the optimum distance and properly positioned as determined by the unstretched length of the flexible strap, he may expand further against the resistance of the elastic, thus flexing the appropriate muscles and joints. The cuff assemblies are worn on the student's wrists or ankles, and have "D" rings providing an attachment point for the swivel connectors at opposite ends of the flexible strap. The cuff assemblies are made up of an outer cuff, preferably constructed of Velcro material, and an inner cushioning liner, preferably made of neoprene rubber and are attached to the respective limb by wrapping around and attaching the outer cuff to itself by means of the Velcro material. The swivel connectors allow for the switching of karate positions while wearing the device without binding.

15 Claims, 4 Drawing Sheets

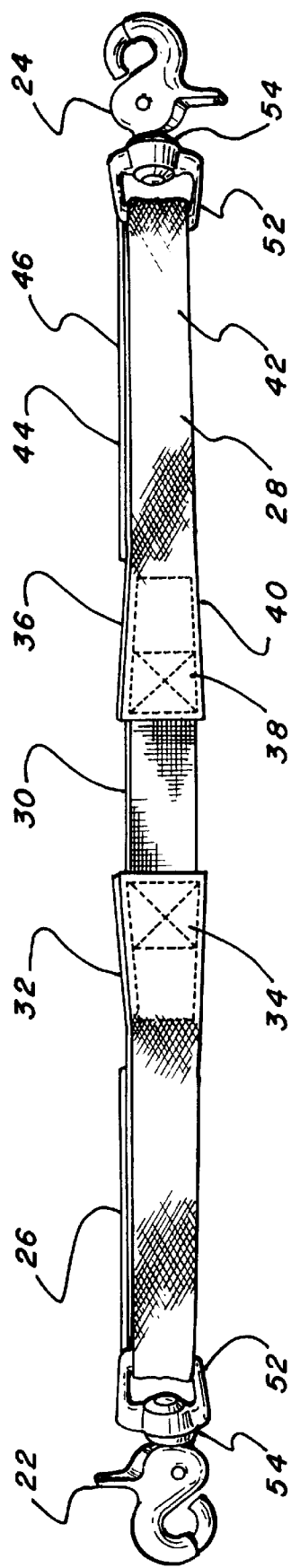
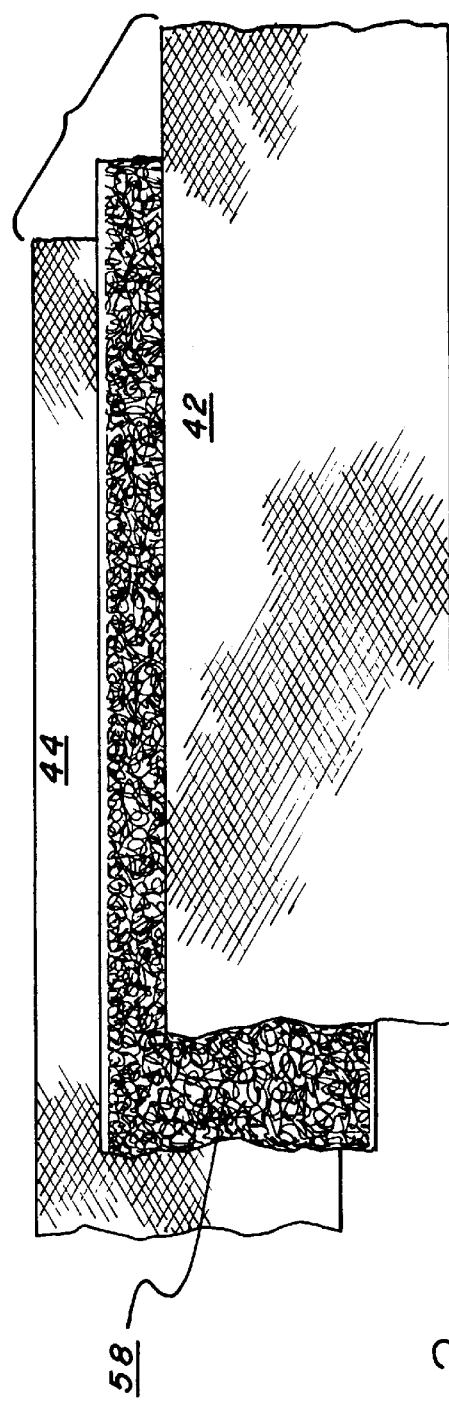
FIG. 2
FIG. 2a

LIMB POSITIONING DEVICE

BACKGROUND OF THE INVENTION

1. Field of the Invention

The present invention relates to devices for assisting an individual in the position of limbs for training in sports such as karate. More specifically the present invention relates to a strap device to be worn on the arms or legs which limits the distance between the arms or the legs and thus is useful in teaching the appropriate stance for a particular karate position.

2. Discussion of the Prior Art

Stance restricting devices to be worn on an individual's legs for training purposes are known in the prior art. Quigly, in U.S. Pat. No. 5,016,885, teaches a golf training device employing Velcro straps to be worn on the legs which restricts the stance to detect imbalances in the golf swing. Gallagher, in U.S. Pat. No. 4,757,995, provides a similar stance limiting device to be worn between the legs for use in improving the stance while training in the hitting of a baseball.

The prior devices have certain limitations, particularly when used for karate training since once they are adjusted for a particular limb separation, they provide no stretch capability. It has been found that the addition of a limited stretch capability to the stance position device not only provides for the limiting of the length of a stance, but aids in properly stretching related joints and muscle groups and helps properly align the limbs while assuming karate positions. For example, while the proper distance in a front stance is important, it is equally important that the ankles be bent forward, which is accomplished by assuming a stance that is at the limit of the unstretched length of the device and then bending the ankles so as to stretch the elastic portion of the device. The device provides desired tension against the bending action of the ankles. In general, it is known to be desirable that, in addition to the assumption of proper stance distance, the karate student properly flexes his ankles, knees, and hip joints. Also, when executing blocks and punches, it is important that the shoulder joints and elbows are properly positioned and the chest and back muscles are properly flexed. The present invention, being adaptable to being worn either on the arms or the legs, allows for both proper relative positioning of the limbs for a particular position or movement, but also provides for the desired flexing of muscles against the tension of the limited stretch capability of the inventive device.

SUMMARY OF THE INVENTION

It is an object of this invention to provide a stance limiting device to be worn by an individual such as in training for karate having both a stance length-determining capability and a limited stretch capability for flexing muscles and joints.

It is a further object of the invention to provide a combination stance limiting and muscle flexing device having detachable adjustable cuffs for convenient fit on wrists or elbows, and ankles or knees.

It is yet a further object of the invention to provide a combination stance limiting and muscle flexing device having cuffs with removable cushioning liners.

It is a still further object of the invention to provide a combination stance limiting and muscle flexing device which is easily adjusted in length for differing stances and individuals of different size.

Additional objects, advantages, and novel features of the invention will become apparent to those skilled in the art upon examination of the following description or may be learned by practice of the invention. The objects and advantages of the invention may be realized and attained by means of the instrumentalities and combinations particularly pointed out in the appended claims.

To achieve the foregoing and other objects, and in accordance with the purpose of the present invention, as embodied and broadly described herein, the present invention may comprise a combination stance limiting and muscle flexing device particularly useful in karate training. The device consists of a flexible strap which is adjustable in total length, connected at opposite ends by means of swivel connectors with cuff assemblies to be worn on the legs or arms of an individual. The flexible strap is made up of two length-adjustable portions connected by an elastic portion. The length-adjustable portions form loops at their ends remote from the elastic portion to receive the swivel connectors. These loops may be adjusted in size, preferably by folding the strap material over on itself at selected positions along the body of the strap material. The strap material is conveniently made of Velcro material which easily attaches and detaches to allow for easy adjustment. The overall length of the flexible strap is determined by the length of these end loops thus formed. The elastic portion of the strap allows a limited stretch capability of about two inches. The purpose of the elastic portion is to give the student a point at which to expand the appropriate muscles and joints against the resistance of the elastic. Once the student's limbs are at the optimum distance and properly positioned as determined by the unstretched length of the flexible strap, he may expand further against the resistance of the elastic, thus flexing the appropriate muscles and joints. The cuff assemblies are worn on the student's arms or legs, primarily at the wrists or ankles, and provide an attachment point for the swivel connectors at opposite ends of the flexible strap. The cuff assemblies are made up of an outer cuff, preferably constructed of Velcro material, and an inner cushioning liner, preferably made of neoprene rubber. The cuff assemblies are conveniently attached to the respective limb by wrapping around and attaching the outer cuff to itself by means of the Velcro material. The outer cuff has a "D" ring for easy attachment and detachment of the flexible strap. The swivel connectors allow for the switching of karate positions while wearing the device without binding.

BRIEF DESCRIPTION OF THE DRAWINGS

The accompanying drawings, which are incorporated in and form part of the specification, illustrate an embodiment of the present invention and, together with the description, serve to explain the principles of the invention.

FIG. 2 is a detail of FIG. 1, illustrating the flexible strap, including the elastic portion and the length-adjustable portion, with attached swivel trigger hook.

FIG. 2A is a detail of FIG. 2 illustrating the preferred manner in which the length-adjustable portion is attached to itself when folded over to form a loop.

DETAILED DESCRIPTION OF THE INVENTION

In the study of karate it is important that the distance between the feet be constant for the ideal stance. It is often hard for a practitioner to determine if his stance is properly wide and long enough. Even experienced students periodically move out of the optimum distance for their body type and flexibility. It is also important that, in addition to the proper distance, that the student properly flexes the ankles, knees, and hip joints. When executing blocks and punches, it is important that the shoulder joints and elbows are properly positioned and the chest and back muscles are properly flexed.

The importance of flexing the ankles has been commented upon by Master T. Okazaki in *The Textbook of Modern Karate,* at page 70 where it is stated: "Achieving the outside tension on the knee requires use of the ankles as well as the hips." Master Nakayama in *Best Karate Fundamentals,* at page 56 states: "The ankle although bent must be firm; otherwise the stance will be weak."

The device of the present invention allows new students to feel the proper relationship, and experienced students to check the status, of their stance. The length is adjustable to either a length based on classic standard ratios(e.g. two times shoulder width for front stance) or a custom length determined by the instructor. The device is also used attached to the wrists to properly position the arms in blocking and punching movements. When used in blocking positions, it encourages the user to expand the chest and hip, putting the proper muscles into play.

The device of the present invention also allows the student to visually check the proper width and distance of a stance and the proper placement of the arms. For example, when executing the front stance, the proper distance is normally two shoulder lengths long and one shoulder length wide. Once the student gets to the end of the distance part, he can visually observe if the strap is straight, indicating that the stance is not wide enough, or if it is diagonal, showing the proper width.

It normally takes a student a period of about two years to "find", or for his body to memorize, the proper positions for various karate stances without the use of a training device as in the present invention. The inventive device cuts down the time necessary for this process, significantly. Once a student has achieved a stable and correct stance, he can effectively study proper movement. If an advanced student does not have a correct stance, he often must return to relearn proper stance position. By using the inventive device, a student can be assured that he has developed a solid foundation and will advance more quickly in training.

Figure 1:
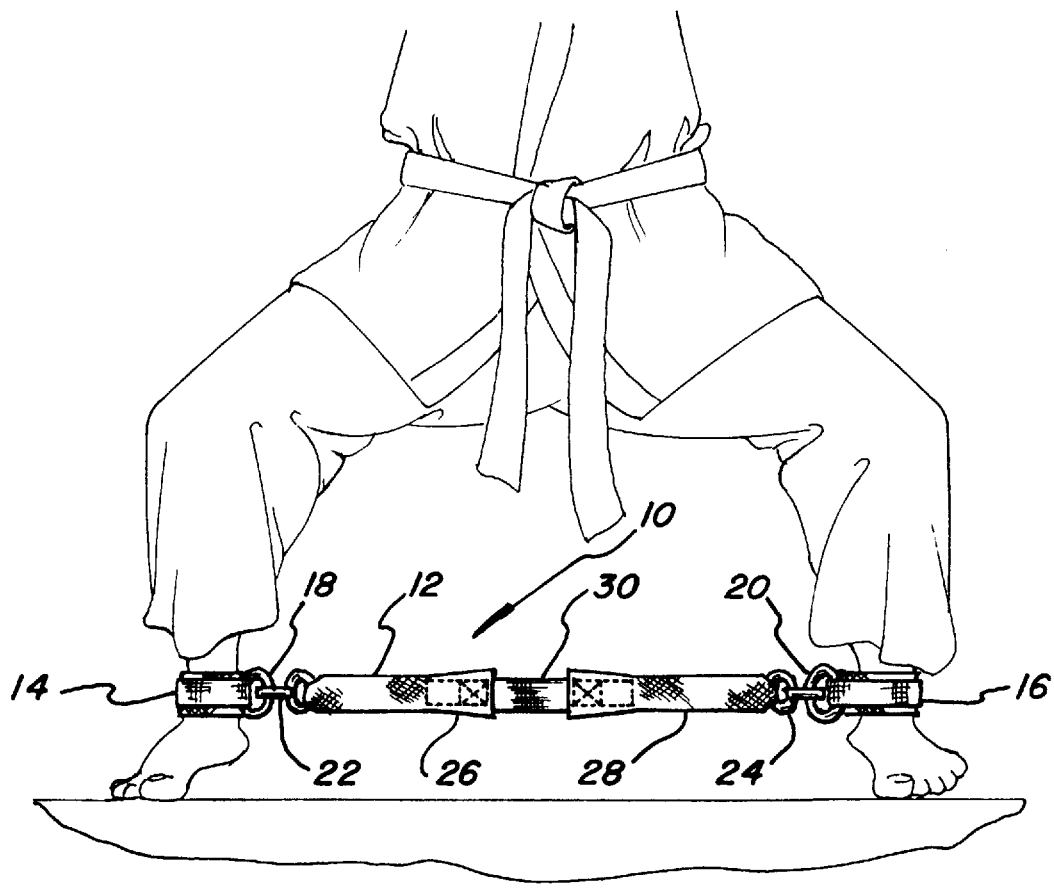
FIG. 1 is a depiction of the present invention being worn on the ankles of an individual in a karate stance.

Referring to FIG. 1, positioning device 10 includes flexible strap 12 and cuff assemblies 14 and 16. Attachment "D" rings 18 and 20 are located on cuff assemblies 14 and 16, respectively. Flexible strap 12 is detachably connected at opposite ends with cuff assemblies 14 and 16 by swivel trigger hooks 22 and 24 which engage "D" rings 18 and 20, respectively. Flexible strap 12 is made up of length-adjustable strap portions 26 and 28, permanently affixed to an elastic strap portion 30 at opposite ends thereof. Swivel trigger hooks 22 and 24 are adjustably engaged with adjustable strap portions 26 and 28 so as to remain at opposite ends of flexible strap 12 at all times.

Referring to FIG. 2 there is shown the flexible strap 12 of the present invention with swivel trigger hook 24 in more detail, wherein length-adjustable strap portion 28 is permanently attached at its fixed end 32 to an end 34 of elastic strap portion 30 such as by sewing. Length-adjustable strap portion 28 is permanently attached at its fixed end 36 with an opposite end 38 of elastic strap portion 30 such as by sewing. Length-adjustable strap portion 28 includes attachment portion 40 and loop portion 42, terminating in adjustable end portion 44. As illustrated, length-adjustable strap portion 28 is folded over itself at loop portion 42 to form loop 46. Adjustable end portion 44 can be mounted at selected locations along the body of loop portion 42. As is further seen in FIG. 2, swivel trigger hook 24 includes trigger hook 40, and mounting ring 52 connected at swivel 54. Swivel trigger hook 24 engages loop 46 of length-adjustable strap portion 28 by means of mounting ring 52. As is seen in FIG. 2A, attachment web 58 is so constructed as to engage the inner surface of loop portion 42 so as to secure it to itself when folded over to form loop 46. Attachment web 58 is preferably constructed of double-sided Velcro hook material, and length-adjustable strap portion 28 is constructed of double-sided Velcro loop material to form easily detachable bonds therebetween.

Figure 3:
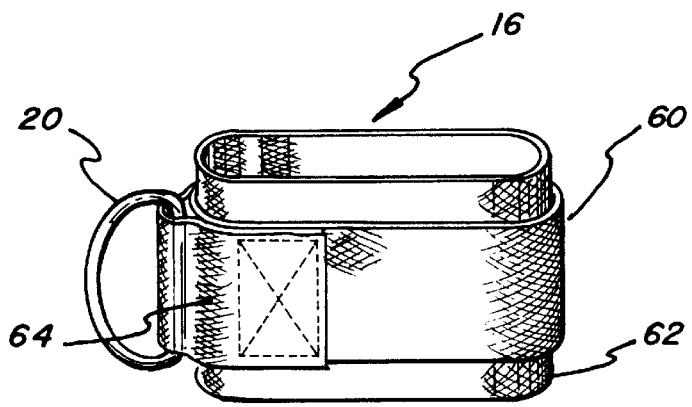
FIG. 3 is a depiction in elevation of the cuff assembly of FIG. 1.

Referring to FIG. 3 there is shown cuff assembly 16 as it is intended to be worn on a human limb. Cuff assembly 16 is made up of outer cuff web 60 and inner cushioning web 62. "D" ring 20 is attached to the outer surface of outer cuff web 60 by strap 64 affixed at opposite ends to the outer surface of outer cuff web 60 as by sewing.

Figure 3A:
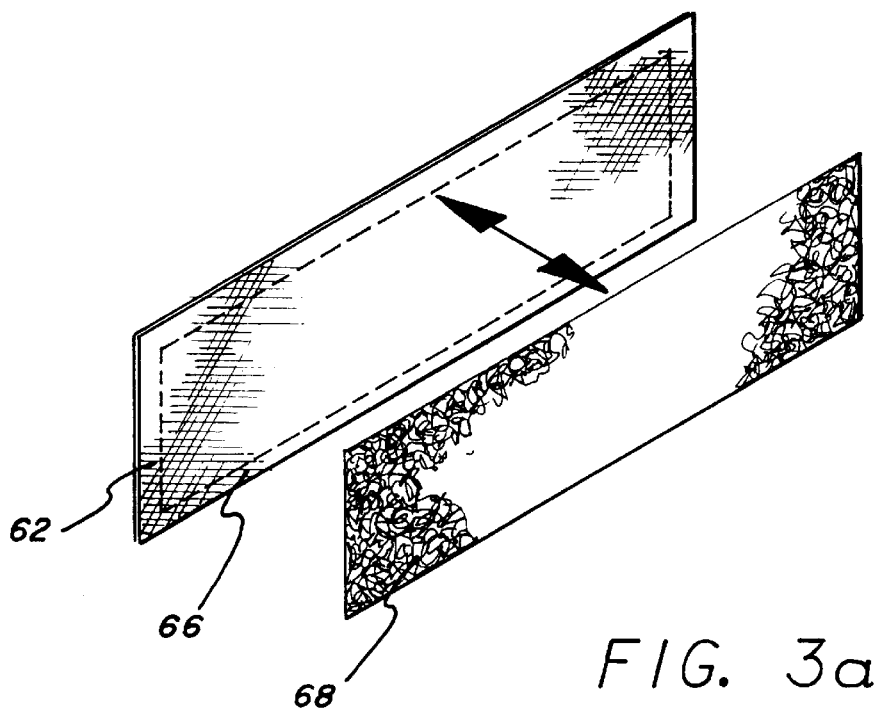
FIG. 3A is a detail drawing showing the inner cushion element of the cuff assembly of FIG. 3 in an unrolled configuration.

Referring to FIG. 3A there is shown a detail drawing of the inner cushion web 62 of FIG. 3, which is made up of cushion web portion 66 and cushion web attachment portion 68. Web portion 66 is preferably constructed of neoprene rubber of about 2½ inches width and of suitable length and thickness to fit around a human limb and provide adequate cushioning thereto. Cushion web attachment portion 68 is constructed of "hook" Velcro material and is suitably sized to provide for attachment to the inner surface of outer cuff web 60. Cushion web attachment portion 68 is suitably affixed to the outer surface of cushion web portion 66 such as by sewing.

Figure 3B:
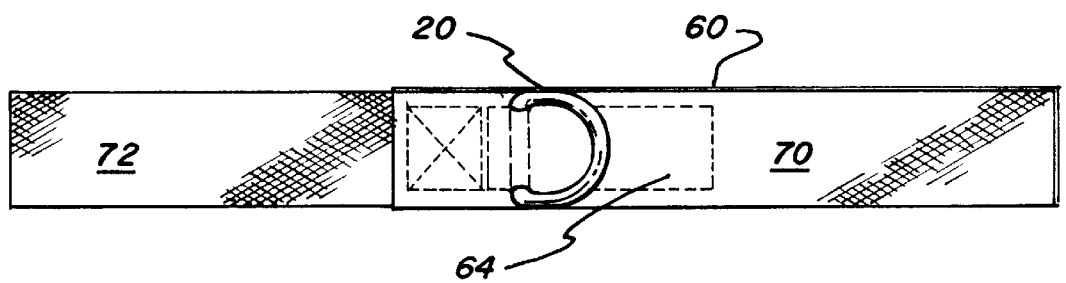
FIG. 3B is a detail drawing showing the outer cuff element of the cuff assembly of FIG. 3 in an unrolled configuration.

Referring to FIG. 3B, outer cuff web 60 includes double-sided loop portion 70 and single sided hook portion 72. "D" ring 20 is mounted on the outer surface of double-sided loop portion 70 by strap 64. Double-sided loop portion 70 has a Velcro loop surface on both its inner and outer surfaces. Single-sided hook portion 72 has a Velcro hook surface on its inner surface such that when outer cuff web 60 is placed around a human limb, the hook surface of single-sided hook portion 72 engages the outer loop surface of double-sided loop portion 70 to form a detachable bond therebetween. The Velcro hook surface of cushion web attachment portion 68 of inner cushion web 62 (See FIG. 3A) detachably bonds with the Velcro loop surface on the inner surface of double-sided loop portion 70 of outer cuff web 60 to form a single cuff assembly 16. Cuff assembly 14 may be described identically to cuff assembly 16.

Figure 4:
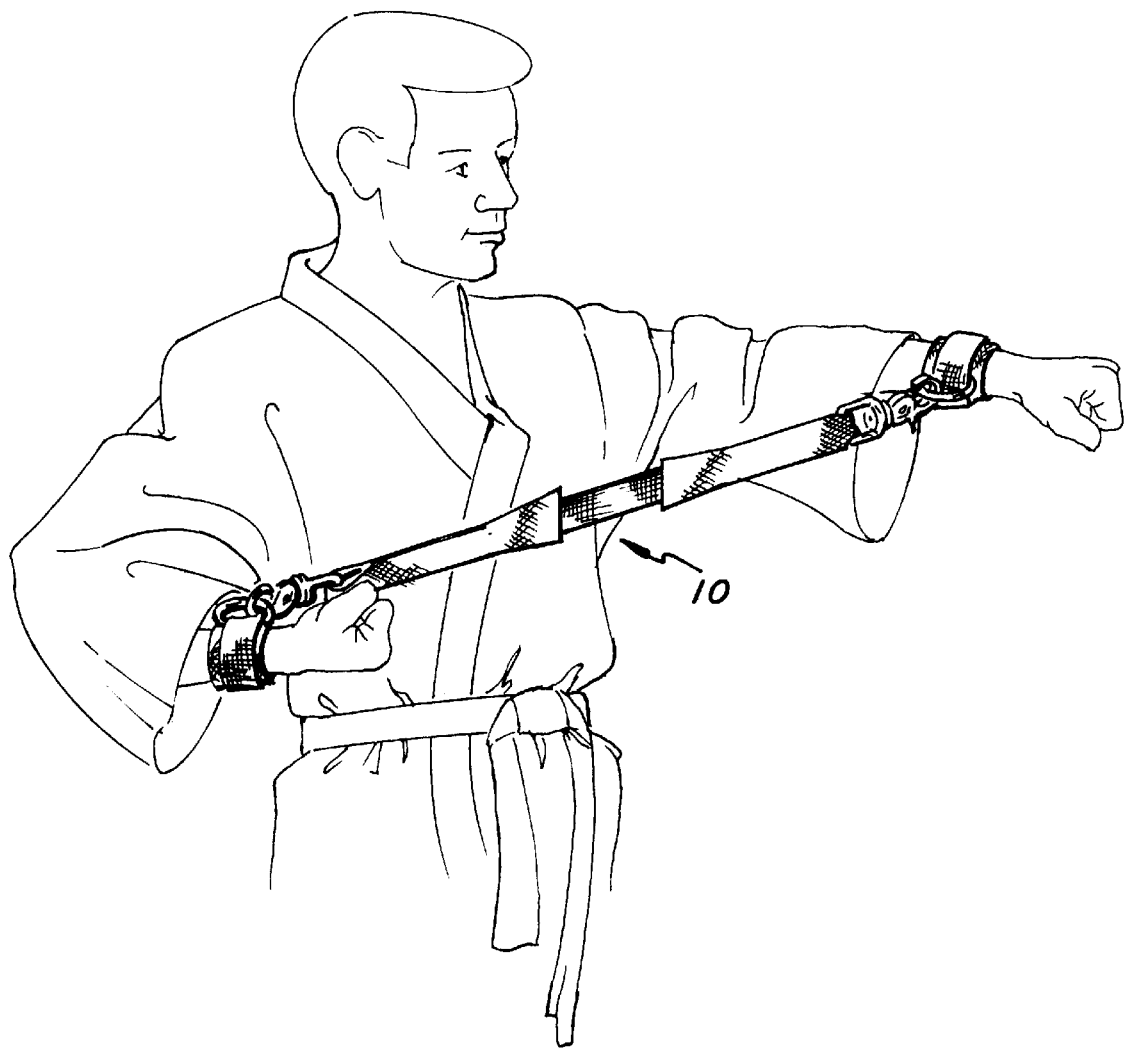
FIG. 4 is a depiction of the present invention being worn on the wrists of an individual in a karate position.

Referring to FIG. 4, there is shown the positioning device 10 worn on the wrists of an individual for positioning the arms for proper blocking and punching.

In operation, cuff assemblies 14 and 16 are placed onto a human users' limbs by wrapping each cuff assembly around the respective limb, and by attaching the Velcro single-sided hook portion 70 at an appropriate location on the outer surface of double-sided loop portion 72 of outer cuff web 60 so as to snugly fit the user's limb. Opposite ends of flexible strap 12 are attached to "D" rings 18 and 20 by means of swivel trigger hooks 22 and 24, respectively. The overall length of flexible strap 12 can be adjusted by adjusting the length of length-adjustable portion 28 by selective placement of adjustable end 44 along the body of loop portion 42 through use of attachment web 58. Length-adjustable strap portion 26 can be adjusted for length in an identical manner to length-adjustable strap portion 28. Elastic portion 30 allows for a limited amount of extension or "stretch" in the strap for purposes explained in more detail below.

Although the size of the flexible strap 12 may be varied for large adults and for children, it is preferably about 33 inches in total length and is made of two fifteen inch straps of one inch wide C-folded "loop" Velcro material joined in the center with a five inch length of one inch wide elastic (see FIG. 2) that is sewn into the C-fold Velcro about one inch on each side so that only about three inches of the elastic is visible. The C-fold Velcro is commercially available and consists of two Velcro strips, one being about one inch in width, and a second being about one and an half inches wide that is formed around the edges of the one-inch portion in the form of a "C" such that about one quarter inch of the wider material folds over each edge of and surrounds the one inch strip. The two pieces of Velcro are sewn top and bottom joining the strips at both edges. The stitches of this stock material can be removed to allow the elastic portion 30 to be inserted between the folds and sewn between the two Velcro straps. Both ends of length-adjustable portions 26 and 28 of flexible strap 12 are designed to be inserted through the attaching ring of ¾ inch swivel trigger hooks such as ring 52 of hook 24 and loop back to the main part of the main body of the strap, the wide portion of the strap being joined together by a piece of double-sided one inch wide "hook" Velcro 58(See FIG. 2A). The hook Velcro piece 58 attaches between the outgoing(to the swivel ring 52)) and returning(from the swivel ring 52) lengths of strap in the manner of a sandwich at a selected position so as to maintain a desired adjustment and thus overall length of flexible strap 12.

The overall length of flexible strap 12 is adjustable by adjusting the length-adjustable portions 26 and 28 in a similar manner. The swivel trigger hooks allow attachment of the flexible strap 12 to cuff assemblies 14 and 16 by means of "D" rings 18 and 20. The elastic portion of flexible strap 12 allows a limited stretch of about two inches from a relaxed length of about 3 inches to a stretched state of about 5 inches. The elastic portion of flexible strap 12 in its relaxed state makes up about 12 percent to 15 percent of the overall length of the flexible strap as worn by the user, depending upon the desired overall adjusted length.

The cuff assemblies 14 and 16 are intended to surround limb joints and are provided with material to prevent chaffing upon movement. The cushioning material is removable for cleaning by means of Velcro strips that attach the anti-chaffing portion 62 to the outer cuff. Each outer cuff has a "D" ring for attachment to the swivel trigger hook of the flexible strap 12 and is fastened around the joint with Velcro or equivalent fasteners. Each cuff assembly is made, for example, from one and one-half inch wide C-fold loop Velcro straps (See description, above, for C-fold Velcro straps). One portion of the assembly is constructed of double-sided loop Velcro, while the remaining portion is constructed of one-sided "hook" Velcro, allowing the outer cuff to be fastened securely around the limb joint by wrapping the cuff upon itself, and through the attached "D" ring, if necessary. The length of outer cuff 60 may vary, but is typically about twenty inches in length, overall. About nine inches from one end, a one and one-quarter inch "D" ring is attached to the outer cuff 60 by an additional piece of nylon strapping material 64. Inner cushioning element 62 is constructed from neoprene rubber, for example, which is preferably about two and one-half inches wide, with a one and one-half inch strip 58 of "hook" Velcro sewn into the center of its length for attachment to the inner side of the double-sided loop Velcro portion of outer cuff 60. Inner cushioning element 62 is positioned in use between the skin of the limb joint and the outer cuff by the aforementioned Velcro attachment.

The purpose of the elastic portion 30 of flexible strap 12 is to give the student user a point at which to expand the appropriate muscles and joints. Once the student's limbs are at the optimum distance as achieved with the elastic in the relaxed state, the student exerts force to expand the elastic portion, thus involving the appropriate muscles and joints to obtain the desired flexing, thereof. Neither the length-adjustable portions or the elastic portion of the flexible strap is intended to withstand violent force, but the strap is intended to act substantially as a guide.

The swivel trigger hooks 22 and 24, located at the extremities of the flexible strap 12, allow the flexible strap to be detached for comfort and convenience and to allow further training without the stance positioning feature of the invention. The swivels allow the student to move in the stance from full extension, to movement, and to full extension without binding. The triggers allow the flexible strap to be easily attached or detached to the cuff assemblies and thus allows the student to continue a training session without the strap while avoiding the need to remove the cuff assemblies. Spring loaded trigger hooks are preferred, but the use of equivalent devices such as snap hooks are contemplated by the invention.

The invention is further illustrated by the following examples:

EXAMPLE 1

In the case of a forward-type stance, where the inventive device is worn on the student's ankles, once the flexible strap is at a maximum distance without pressure, the student observes the angle of the strap to insure that the width is appropriate, he bends his front knee, twists his hips forward, stretches his groin muscles, and locks his rear leg, which stretches the ankles slightly more and puts the strap to its physical limit.

EXAMPLE 2

In the application to the back stance, where the inventive device is worn on the student's ankles, the student extends his feet to the maximum distance of the strap without pressure, then bends his back knee down and out(back) and the front knee slightly forward, forcing the elastic portion to its physical limit. By visually inspecting the strap he can determine if the width of the stance is proper while maintaining the stance.

EXAMPLE 3

In the application to the side stance, the cuff assemblies are attached below or above the knees, which puts the knees at the proper separation. The cuff assembly can be attached to the ankles so that the proper distance is first obtained between the feet. The student then pushes his knees down and out against the ankles, stretching the elastic, thus lowering the stance and stretching the proper muscle groups.

EXAMPLE 4

In the application to movement in stances, the cuff assemblies are attached to the ankles. The student must memorize the proper distance to travel (end of the unstretched strap) and then expands the elastic into the proper stance. If the student goes too far, the straps may pull apart. If too short, the elastic will not be stretched. Speed can be gauged by the ability to keep the flexible strap from hitting the floor during the movement.

EXAMPLE 5

In the application to the rising block, the cuff assemblies surround the wrists and the flexible strap places the draw hand and blocking hand in proper alignment. The stretching action again causes the chest and back muscles, as well as the hip, to work in their proper relationship. The level and angle of the flexible strap helps indicate any improper alignment of the arms and hands.

EXAMPLE 6

In the application to the knife hand block, the cuff assemblies surround the wrists and the flexible strap puts the draw hand and blocking hand in proper alignment. The stretching action again causes the chest and back muscles, as well as the hip, to work in their proper relationship. The level and angle of the flexible strap helps indicate any improper alignment of the arms and hands.

EXAMPLE 7

In the application to the outside/inside block, the cuff assemblies surround the wrists and the flexible strap puts the blocking and draw hand in proper relative position. The stretching opens the chest and uses the back muscles. The elastic portion also allows the student to practice muscle expansion/contraction at appropriate points. The level and angle of the strap helps indicate any improper alignment of the arms and hands.

EXAMPLE 8

In the application to punching, the cuff assemblies are attached to the wrists. The flexible strap may be deployed behind the body and/or in front of the chest, depending on the area of concentration. In using the strap behind the back, the student is forced to use the punching and draw hand simultaneously. The length of the flexible strap forces the student to keep the shoulder down and tense the appropriate muscles in the shoulder and back. The strap keeps the student from overextending the punching arm, which may give greater distance to the punch, but decreases the power obtained from a good connection with the body. Using the device in the front helps develop proper timing, i.e., the punching hand and draw hand tense and move simultaneously. Use around the back helps develop the draw hand.

EXAMPLE 9

In the application to the front kick, the cuff assemblies surround the ankles. The flexible strap helps the student correctly keep his knee up ant the lower part of his kicking leg under his knee and close to the upper part of the leg. The movement is done up to the point of the bottom part of the leg arcing into the kick.

EXAMPLE 10

In the application to the roundhouse kick, the cuff assemblies surround the ankles. The flexible strap forces the student to keep the leg and body positioned correctly and forces the student to pivot prior to arcing the lower part of the leg into the kick.

EXAMPLE 11

In the application of the side-snapping kick, the cuff assemblies surround the ankles. The flexible strap forces the student to keep his feet sliding on the ground (to avoid tripping) and shows the student the correct position of the lower leg prior to the arcing of the lower leg into the kick.

EXAMPLE 12

In the application to shifting techniques, the cuff assemblies surround the ankles. As the student shifts from position to position and from stance to stance, he is forced to bring his legs inward between shifting. He can gauge the speed of his movement by trying to keep the flexible strap from hitting the ground during the movement.

The particular sizes and equipment discussed above are cited merely to illustrate a particular embodiment of this invention. It is contemplated that the use of the invention may involve components having different sizes and shapes as long as the principle, the use of an adjustable length strap having a limited elastic stretch capability for placement on human limbs to position them relative to each other and to provide for flexing of related muscles, is followed.

I claim:

1. A device for the relative positioning of human limbs comprising:

A. a flexible strap having first and second ends;

B. a cuff assembly located at each of said first and second ends; and

C. means for fastening said cuff assemblies to each of said first and second ends, respectively; and D. said flexible strap comprising at least one relatively inelastic length-adjustable portion and at least one elastic portion linearly attached thereto; and E. said elastic portion making up about 12 percent to 15 percent of the total length of said flexible strap;

whereby each of said cuff assemblies are adapted to be worn on two limbs of a human so as to maintain those two limbs positioned in a specified spaced relation to each other.

2. The device of claim 1 wherein said flexible strap comprises two of said length-adjustable portions separated by one of said elastic portions so assembled in end to end relationship as to form a single flexible strap extending between said cuff assemblies.

3. The device of claim 2 wherein said elastic portion is an elastic web characterized by having a predetermined maximum extension capability upon application of tension at either end thereof.

4. The device of claim 3 wherein said predetermined maximum extension is about two inches.

5. The device of claim 1 wherein said length-adjustable portion of said flexible strap comprises a loop portion and an attachment portion, said attachment portion being affixed to an end of said elastic portion, and said loop portion being held by said cuff assembly fastening means.

6. The device of claim 1 wherein said cuff assembly fastening means comprise a trigger hook and a ring, said ring being affixed to said cuff assembly, said trigger hook having a spring-loaded hook portion being adapted to selectively engage and disengage said ring, said trigger hook further comprising a ring portion adapted to slidingly engage said loop portion of said length adjustable portion of said flexible strap.

7. The device of claim 6 wherein said trigger hook is a swivel trigger hook and wherein said ring portion and said hook portion are swivelably engaged.

8. The device of claim 5 wherein said length-adjustable portion is formed from an elongated web having a body portion with first and second end portions, said first end portion and said body portion forming said attachment portion, said second end portion being attached at selected locations along said body portion forming said loop portion, whereby the overall length of said length-adjustable portion and, thus said flexible strap, is determined by the selected location of attachment of said second end to said body portion.

9. The device of claim 8 wherein said length-adjustable portion further comprises an attachment web having first and second sides, said first and second sides having first attachment means thereon, said body portion of said length-adjustable portion and said second end portion having second attachment means on at least one surface thereof such that said first attachment means on said attachment web interacts with said second attachment means on said body portion to secure said second end portion to said body portion at said selected location forming said loop portion.

10. The device of claim 9 wherein said first attachment means is one of Velcro loop material or hook material and said second attachment means is the other of Velcro loop material or hook material.

11. The device of claim 1 wherein said cuff assembly comprises an inner cushion web and an outer cuff web, said inner cushion web being of a cushioning rubber material and adapted for wrapped engagement with a human limb, said outer cuff web having inner and outer surfaces, said outer cuff web surrounding said inner web and having cuff attachment means so as to detachably secure said cuff assembly to said human limb.

12. The device of claim 11 wherein said attachment means comprises an overlapping portion of said outer web selectively attachable to the remaining portion of said outer web so as to secure said web around said human limb.

13. The device of claim 12 wherein said attachment means comprise one of Velcro hook or Velcro loop material located on the inner surface of said overlapping portion, and the other of Velcro hook or Velcro loop material located on the outer surface of said remaining portion.

14. The device of claim 12 further comprising Velcro material located on an outer surface of said inner cushion web so as to attach to the inner surface of said outer cuff web to form said cuff assembly.

15. A device for the relative positioning of human limbs comprising:

A. a flexible strap having swivel trigger hooks located at first and second ends thereof; and B. a cuff assembly located at each of said first and said second ends and having a ring affixed thereto; and C. said swivel trigger hooks attached to said first and said second ends being detachably engaged with said rings affixed to said cuff assemblies; and D. said flexible strap comprising a center elastic portion with two ends having an extended length of about 5 inches and a unextended length of about 3 inches, and a length-adjustable portion of relatively inelastic material fixedly attached at each end of said elastic portion; and E. said length-adjustable portion being capable of forming a loop by attachment of a remote end to selected location along said length-adjustable portion to form a loop of desired size and thus determine the overall length of said flexible strap;

F. said elastic portion making up about 12 percent to 15 percent of the overall length of said flexible strap.

* * * * *